United States Patent [19]

Leonardi

[11] Patent Number: 4,907,580

[45] Date of Patent: Mar. 13, 1990

[54] EYELID SPLINT WITH REPLACEABLE PAD

[76] Inventor: David Leonardi, 2320 Plaza del Grande, Las Vegas, Nev. 89102

[21] Appl. No.: 261,339

[22] Filed: Oct. 24, 1988

[51] Int. Cl.$^4$ ............................................. A61F 13/12
[52] U.S. Cl. ................................................... 128/163
[58] Field of Search ...................... 2/15, 440; 128/155, 128/163, 857, 858, 889, 890, 893, 894, 156; 604/332, 345

[56] References Cited

U.S. PATENT DOCUMENTS

| | | | |
|---|---|---|---|
| 1,917,117 | 7/1933 | Hines | 128/163 |
| 2,342,840 | 2/1944 | Cadous | 2/15 |
| 2,389,223 | 11/1945 | Werner | 128/163 |
| 3,300,786 | 1/1967 | Rosenvold et al. | 128/858 |
| 3,339,206 | 9/1967 | Daley | 128/163 |
| 4,122,847 | 10/1978 | Craig | 128/858 |
| 4,473,370 | 9/1984 | Weiss | 128/163 |
| 4,635,625 | 1/1987 | Teeple | 128/163 |
| 4,649,908 | 3/1987 | Ghaly | 128/858 |
| 4,677,974 | 7/1987 | Leonardi | 128/163 |
| 4,790,031 | 12/1988 | Duerer | 128/858 |

*Primary Examiner*—Richard J. Apley
*Assistant Examiner*—N. Paul
*Attorney, Agent, or Firm*—Quirk, Tratos & Roethel

[57] ABSTRACT

An eyelid splint has a structural backing member having head-encircling straps having adjustable strap fasteners, such as Velcro®. A flexible resilient pad is removably mounted to the inner surface of the backing member, which is preferably concave. The pad is attached to the backing member by means of an adhesive having a low-peel adhesion strength (i.e., generally less than 20 oz.) enabling easy removal and replacement of the pad.

19 Claims, 2 Drawing Sheets

EYELID SPLINT WITH REPLACEABLE PAD

BACKGROUND OF THE INVENTION

This invention relates to a device for immobilizing an eyelid of an injured eye by means of an eyelid splint. In particular, it relates to a shield attached to a head-encircling strap, with the shield having a thick, resilient pad attached to its interior surface by means of a "low-peel" adhesive.

Eyelid splints having backing members attached to foam pads are described in my previous U.S. Pat. No. 4,677,974 and U.S. Pat. No. 4,727,869, each entitled "Method And Apparatus For Immobilizing An Eyelid". The eyelid splints described in these patents have a variety of uses in the medical field, generally being used in cases in which the eyelid must be maintained in a fixed, closed position to permit healing. Eyelid immobilization is indicated for corneal abrasions, corneal burns, keratitis, and following corneal or cataract surgery. Eyelid immobilization is also helpful to prevent injuries to the cornea from drying when a patient is unable to close the eyelid due to neurologic deficiencies caused by e.g., Bell's palsy, stroke, head injury, or coma. The products described in my previous patents include eyelid splints which are mounted on the head of the patient by a pair of head-encircling straps. The straps are elastic, and the lengths are adjustable, in order to adjust the pressure of the splint against the eyelid. The pads are adhered to an inner surface of a backing shield and consist of a thick, resilient foam which, upon compression, assumes the shape of the eye socket. Pressure on the eyelid is adjusted through the adjustment of the strap lengths.

In my co-pending patent application Ser. No. 07/111,809, filed Oct. 21, 1987, entitled "Tapeless Eye Shield Apparatus", the product which is the subject of that application is a generally conventional shield member having head-encircling straps and is designed to avoid the necessity of taping an eye shield to the face of a patient. Eye shields, which differ from splints in that they are not designed to maintain the eyelid in a closed, immobile position, are used simply to prevent accidental injury to the eye and/or exclude light.

It has now been discovered that the construction of an eyelid splint with a flexible, resilient pad having a "low-peel" adhesive for attachment to the inner surface of the backing or shield is highly desirable in certain circumstances. The first advantage is in having the pad "attached" to the splint. This allows removal of the entire device in one piece by either patient or practitioner. This allows repeat exams, showering or application of medicine without having to handle that part of the splint which contacts the eye and is required to be sterile. All eye dressings in current use are composed of 2 to 7 pieces (one or 2 pads plus one to 5 pieces of tape, plus or minus an eye shield). They are very cumbersome to remove and reapply and that part which contacts the eye is easily contaminated.

Construction of the splint with an easily removable pad or "dressing" enables the pad to be easily replaced when wet or soiled without replacing the entire splint. Such a feature is particularly useful for patients having corneal injuries and for post-surgical patients. Corneal injuries are generally treated with antibiotic ointment and an eyelid splint. In general, physicians recommend that the dressing or pad be changed at least every 24 hours as it becomes damp and soiled from the ointment and from eye secretions. Patients may require eyelid splints for at least several days, and occasionally for several weeks. Accordingly, the invention provides the corneal injury patient with a durable (and even washable) backing member and head-encircling straps, both of which are highly desirable features for eyelid splints, but with a dressing that is mountable and detachable from the backing so that it can be replaced quickly and easily. This enables the entirety of the eyelid splint to be reused many times, while replacing the pad as frequently as is desired.

Post-surgical patients often are required to wear an eyelid splint with dressing for one to several days after surgery, and then a protective eye shield with no dressing at bedtime for up to several weeks in order to prevent ocular trauma during sleep. The eyelid splint with removable dressing then enables post-surgical patients to use the splint as described above until a protective eye shield is necessary, at which time the pad or dressing is removed from the interior surface of the splint and the device may then be used as an eye shield as set forth in my co-pending patent application Ser. No. 07/111,809.

According to the invention, the splint comprises a rigid or slightly flexible backing member having a smooth, somewhat concave interior surface, and a pair of adjustable head-encircling straps. The straps are preferably elastic, thereby enabling the wearer to adjust the pressure on the eyelid and to subsequently remove the device and replace the pad. After pad replacement, the splint can be returned into position on the wearer's head without unfastening the straps, thereby obviating retensioning of the straps. A removable foam pad is detachably adhered to the inner surface of the shield by means of a "low-peel" or "permanently removable" adhesive. A preferred method of manufacturing the pad consists of attaching a thin strip of adhesive film to a rear surface of the pad. The film is coated with a "permanent" adhesive on one side, for attachment to the pad, and a low-peel adhesive on the other side for attachment to the shield. The low-peel side is covered with a silicone-coated paper on its surface to protect it until it is ready for attachment to the shield. Adhesives of proper strength are well known and commercially available.

The splint of the invention is easily removed and replaced by a patient or physician since it is a "one-piece" dressing that is easily handled and does not require tape to keep it in place. It is easily adjustable, and can be fit as easily as fitting a hat. In addition to being easily fit and used, however, the device serves a dual purpose since it can be used as an eye shield by removing the pad. Finally, the splint pad is easily replaced with a fresh one without having to purchase an entire new splint.

A number of different head-encircling eye patches are known in the prior art. Examples of eye shields which are designed to cover the eye without contacting the eyelid or eyeball are Wylie, U.S. Pat. No. 591,244, Lush, U.S. Pat. No. 1,161,321, and Werner, U.S. Pat. No. 2,389,223. Various other types of eye bandages which may contain medicine-impregnated pads include Burdick, U.S. Pat. No. 915,738, Robinson, U.S. Pat. No. 1,642,661, Pedersen, U.S. Pat. No. 1,886,725, and Veysey, U.S. Pat. No. 2,024,491. A more complex eye shield which comprises an outer circular frame mounted over a transparent plastic bag filled with fluid to protect and moisten the eye is disclosed in Weiss, U.S. Pat. No. 4,473,370. None of the devices disclosed in the prior art patents show a device designed to immobilize the eyelid and also have a removable dressing pad.

Accordingly, it is an object of the present invention to provide an eyelid splint for immobilizing a patient's eyelid which is self contained as one piece, is comfortable to wear and which has a removable pad member which can be replaced with a new pad member when wet or soiled. It is another object of the invention to provide an eyelid splint having a pad member mounted on an interior surface of a shield by means of a low-peel adhesive. It is yet another object of the invention to provide replacement pads for eyelid splints comprising resilient foam pad members having one surface thereof coated by means of an adhesive having a low-peel strength. A further object of the invention is to provide an eyelid splint which can be used to maintain a wearer's eyelid in an immobilized, closed position, and which also may be used, after removal of the pad member, as an eye shield which protects the wearer's eye from injury yet permits it to open and close at will. These and other objects are achieved by the device of the invention, a specific embodiment of which is described herein.

BRIEF SUMMARY OF THE INVENTION

An eyelid splint comprises a flexible resilient pad having a thickness of about 24 mm, a backing member having a generally concave smooth inner surface, and adhesive means for attaching the pad member to the backing having a low-peel adhesive strength, thus enabling easy removal of used pads from the backing. A pair of elastic straps extend from the backing for encircling the head of a patient and for mounting the pad in fixed position on the patient's eye. The straps each carry interengaging fastening means near their ends, such as Velcro ® fasteners, for enabling the splint to be attached at various adjustable lengths.

BRIEF DESCRIPTION OF THE DRAWINGS

The invention is best understood with reference to the drawings, in which.

DETAILED DESCRIPTION OF A PREFERRED EMBODIMENT

Figure 1:
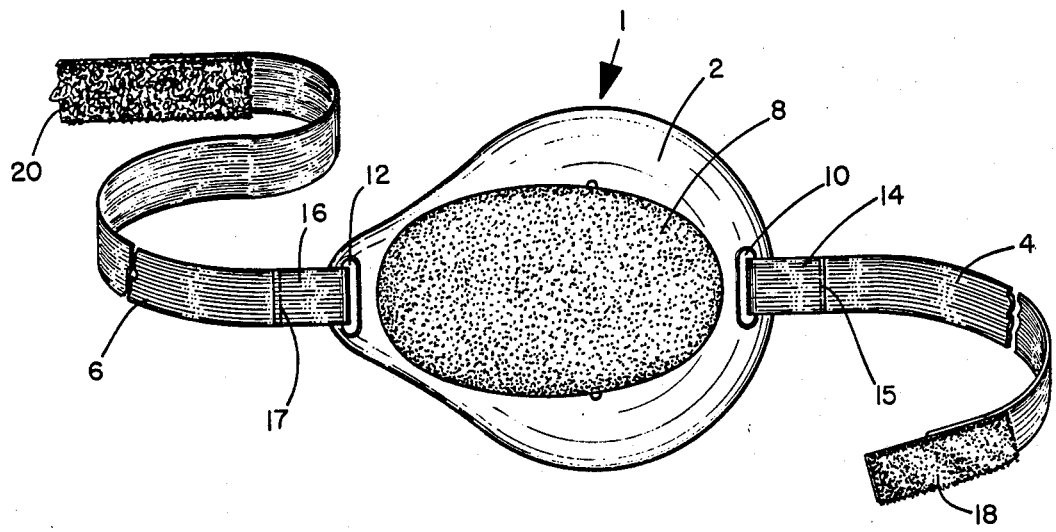
FIG. 1 is a rear view of an eyelid splint having a foam pad mounted thereon.

Referring to FIG. 1, eyelid splint 1 of the invention consists of a backing member or shield portion 2 having an elliptically-shaped foam pad 8 mounted thereon. A pair of head-encircling straps 4 and 6 extend from the backing member and are adapted to encircle the patient's head, as shown in my prior patent U.S. Pat. No. 4,727,869. The straps fasten by patches of interengaging fastening means 18 and 20 carried near end portions of each strap. The straps, which are elastic, are mounted to the backing member by extending through rectangular slots 10 and 12 at opposite sides of the backing member, and are attached by sewing end portions 14 and 16 of the straps as shown at stitching 15 and 17.

Figure 2:
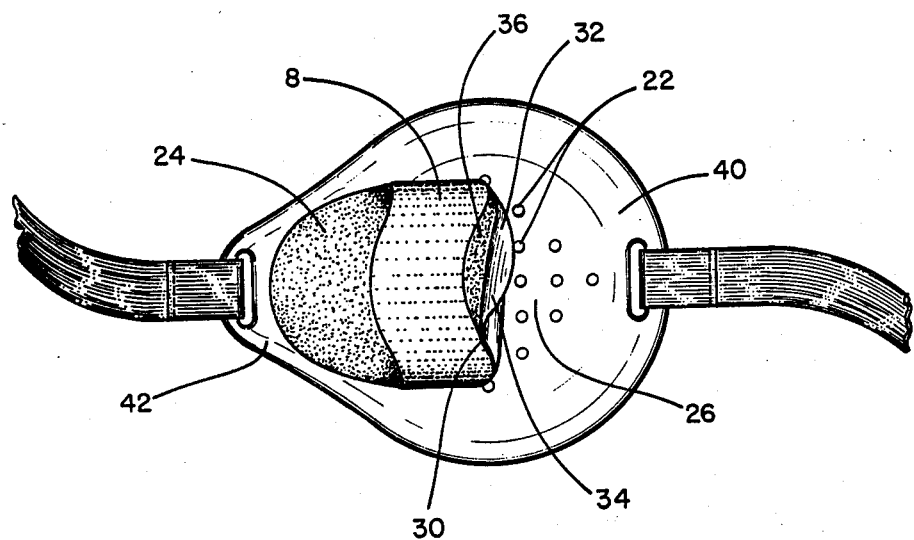
FIG. 2 is a rear view of the splint showing the foam pad in partially removed position, with the mounting film bearing adhesives on each side shown as partially peeled away.

The backing member can be a conventional oval or elliptical eye shield, or a teardrop-shaped shield as shown in FIGS. 1 and 2. Suitable shields are those described in my copending application Ser. No. 07/111,809, filed Oct. 21, 1987, the disclosure of which is incorporated herein by reference. These shields are generally designed to have their exterior margins conform to and bridge across the bony orbital rim of the eye. The shield preferably has a slightly convex exterior surface, and a slightly concave interior surface, the shield being of substantially uniform thickness providing a space between the shield's surface and the eye. If desired, the shield may include a plurality of ventilation holes 22. While these holes or apertures are generally covered up when the device of the invention is used as an eyelid splint, the holes may be used to look through when the device is used as a shield, i.e., with the pad removed. The shield is preferably rigid or semi-rigid, although it may be somewhat flexible if desired, but should be sufficiently rigid to span a patient's facial bone structure surrounding the eye. The structural rigidity of the shield should be at least sufficient for mounting the pad member as described herein. The backing member is preferably fabricated from metal or plastic, enabling the pad to be easily peeled away from the backing. In addition, it is preferred that the shield have a smooth interior surface for the same reason. Cloth backings are not preferred, since the foam pad does not easily adhere well to the cloth, and if a very "sticky" adhesive is used, it is not easy to remove and reapply the pad. Furthermore, cloth pads have no rigidity and cannot be used as a shield apart from the splint.

Figure 4:
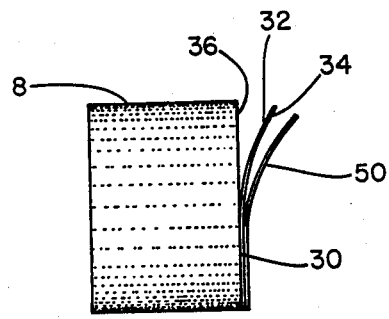
FIG. 4 is a side view of the foam pad showing the mounting film partially removed.

The replaceable feature of the foam pad is enabled by the use of a particular combination of adhesives mounted on a piece of film attached to the back of the pad. As shown in FIG. 2, the foam pad 8 is mounted along a horizontal axis of the interior surface 26 of the shield, being positioned between the end portions 40 and 42 thereof. The pad, which may be foam, cotton, or other resilient material, is laminated to a strip of pressure-sensitive adhesive film 30 having opposing flat surfaces 32 and 34, as shown in FIG. 4. The film may be made of any plastic material, but is generally polyester, and has a thickness of from about 0.3–1.0 mils, preferably about 0.5 mils. The thickness of the film is not critical. The foam side 32 of the film is coated with a "permanent" adhesive, which is designed not to peel off. In the adhesive industry, these "permanent" adhesives are referred to as "general purpose" or "standard peel strength" adhesives. The opposite or shield surface 34 of the adhesive film is coated with an adhesive having a weaker peel strength, termed "low-peel" or "permanently removable". The particular chemical composition of the adhesive is not important, although adhesives generally falling within the definitions of peel strength required by the invention are commonly acrylic adhesives. When the pad is peeled away from the interior surface of the shield, substantially no residual adhesive remains on the shield surface for collection of dust and dirt.

Figure 3:
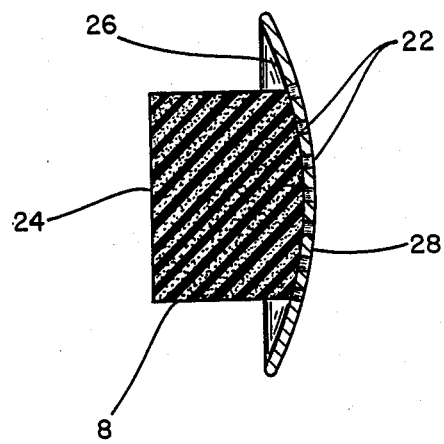
FIG. 3 is a side sectional view of the splint.

FIG. 3 is a side sectional view of the assembled splint of the invention, showing a forward portion of the foam pad adhered in place to the rear surface of the shield, and further showing the slightly concave configuration of the inner surface of the shield. While the splint would be equally operable if the rear surface of the shield were flat, with the foam being sufficiently soft and compressible to conform to the exterior surface of the eye and eyelid, a slightly concave configuration is preferred.

FIG. 4 shows the foam pad in its replacement condition, i.e., prior to being attached to the shield. The adhesive tape 32 and strip of silicone-coated paper 50 which acts as a protective liner for the low-peel adhesive surface 34 are shown in a partially removed condition.

While it is not possible to quantify the required adhesive strength of the strong and weak adhesives which are applied to opposing sides of the adhesive film or tape precisely, the characteristics of permanent and low-peel adhesives are well known in the art. The permanent or general purpose adhesive is generally an acrylic adhesive applied to a thickness of about 1–2.5 mils, preferably about 1.5–2 mils, and having a peel adhesion of at least about 30 oz., and preferably about 50 oz., PSTC-3 MOD. the designation "PSTC-3 MOD" is a testing standard as specified by the Pressure Sensitive Test Council with modification No. 3, which includes the substitution of a 2 mil thickness polyester film for the standard 1 mil film for peel adhesion testing. A shear adhesion, according to test PSTC-7 MOD of over 24 hours is preferred. This test is the Pressure Sensitive Test Council test with modification No. 7, which involves substitution of a 2 mil polyester film for the 1 mil film standard for shear adhesion testing.

The low-peel adhesive is also an acrylic adhesive and has a peel adhesion of less than 20 oz. (PSTC-3 MOD), preferably about 16 oz., and a shear adhesion of over 100 hours. The low-peel adhesive is applied at a thickness of 0.5–1.5 mils, preferably about 0.8 mils. Both the permanent and low-peel adhesives are applied to the polyester tape by reverse roll coating technology. The polyester film is a commercially available product having a tensile strength of 23,000 psi and an elongation of 110%.

The compression pad may be made from a variety of synthetic foams, cotton, or any other synthetic soft material which is not a dermal irritant; the use of a highly resilient foam is substantially preferred. Any commercially available plastic foam, such as polyurethane, polyether, polystyrene, or polyethylene, may be used. A very important feature of the invention is that the foam be sufficiently thick and resilient as to enable the splint to be pressed against the eyelid firmly but without discomfort or risk of damage to the eye. In tests using an intracraneal pressure monitor, it has been found that the optimum amount of pressure exerted on the eyelid at its forwardmost point (i.e., maximum pressure exerted on the lid) should be no less than 23 mm Hg and no more than 40 mm Hg. Higher pressures may result in substantial discomfort and pain to the eye, whereas lower pressures do not enable proper splinting of the lid. In order to maintain the level of pressure within this relatively narrow region, the foam must be highly compressible. For example, when the unit is in place against the eyelid, the pad contours comfortably to the interior portion of the orbital structure surrounding the eye. Therefore, pressure is applied at all points of the lid, preventing its movement. However, if the pressure on the lid at the forwardmost portion of the cornea exceeds 40 mm Hg, the splint will feel uncomfortable, causing patient non-compliance which will result in delayed healing. Accordingly, the thickness of the foam pad is extremely important to the efficacy of the apparatus of the invention. While the thickness will vary with the type and compressibility of the particular pad chosen, the thickness should be a minimum of 7 mm, and is preferably from about 10 to about 30 mm, more particularly 14–25 mm. The use of a thick foam enables a highly compressible foam to be chosen, thereby ensuring maximum patient comfort. A typical example of a preferred foam is one-pound density polyether foam having a compressibility of 5–20 psi, preferably 9–15 psi i.l.d. Denser, less compressible foams tend to result in less comfortable splints. Preferred foam density of 0.7–1.5 pounds/cu. ft., preferably about 1 pound. An example of acceptable foam is Scott M-105-12. The pad is generally of uniform thickness, though it may be contoured slightly concave to fit the front contour of the eye if desired.

The designation "i.l.d." for foam compressibility is an abbreviation for initial load deflection, which is a conventional standard of measurement in the foam industry. The standard procedure for measuring the i.l.d. of a particular foam involves compressing a 50 square inch piece of foam (7.07" square) that is 4 inches thick by a 50 square inch plate to a thickness of 1 inch. The pressure applied to the plate may be varied and is measured in pounds per square inch. The psi i.l.d. of a particular foam is the pressure in psi which compresses a 50 square inch piece of foam from a resting thickness of 4 inches to a compressed thickness of 1 inch.

A variety of lightweight elastic straps can be used. Dozens of materials have been tested for their comfort, including softness of texture, breathability, weight and, most importantly, stretchability. Acceptable materials were those composed of Spandex with one or more of nylon, polyester, and cotton. Elastic cotton materials are preferred because they have a higher coefficient of friction, providing more stability on the head.

Stretchability can be measured by Young's Modulus (YM). Since YM is a function of the cross-sectional area of the material, it can be compensated for by altering the width or thickness of the strap; however, straps less than about 0.8 cm in width tend to be unstable on the head and those greater than 3.0 cm are less comfortable and cosmetically less desirable. Material thickness was generally not critical. The materials which provided a firm comfortable fit in the desirable width range were those whose YM fell between $2.0 \times 10^5$ and $2.0 \times 10^6$, which includes lightweight elastic bands and a few of the heavier elastic materials as used in girdles. An alternate measure is that a force of 1.75 newtons will stretch an acceptable material 5–50% of its length.

Splints of the invention are designed to fit either eye of the patient. The splint is applied by holding the padded side against the closed eyelid, and, while the patient holds the padded backing against his closed eye, bringing the straps around to fasten across the occiput The lateral strap passes across the user's temple and either across the ear lobe or just below the ear; this placement is critical to the stability of the device. The medial strap passes above the contralateral eyebrow, across the forehead, and above the contralateral ear. The Velcro ® ends are then attached to secure the straps. If the splint feels too tight against the eye, it is loosened until comfortable by shortening the length of Velcro ® overlap. Once the patient reports a comfortable fit, he is told to blink both eyes rapidly and repeatedly, and is asked if the splinted eye is able to open. If it can open, the splint is tightened by increasing the overlap of the fasteners. If the patient later wishes to remove the splint by sliding it over his head, for changing the dressing or otherwise, he may do so and replace it without altering the pressure adjustment. Alternatively, where the straps attach in the back, the interior strap can be marked with a pen at the distal edge of the exterior strap in case the patient inadvertently pulls the fastener apart. He can then reattach the Velcro ® ends at the mark under direct visualization and apply it by sliding it over his head to assure the same fit and pressure that was applied by the physician.

While any interengaging fastening means for attaching the straps may be used, such as snaps or buckles, Velcro ® fasteners are preferred because of the ease of attachment and adjustability. Velcro ® fasteners are well known in the fastening industry, and consist of opposing pairs of a large plurality of hooks and loops which interengage releasably when pressure is applied. Alternatively, a single strap may be used having both ends attached to the pad member or backing. In this embodiment, in order to avoid making a multiplicity of sizes of the splint, a relatively long strap is used, and adjustment is effected by using a conventional two-ring adjustment means, or by otherwise fastening (e.g. by stapling) portions of the strap loop together to shorten the strap to the desired length.

While the preferred thickness of the pad has been described as a minimum of 10 mm, a lower pad thickness (e.g., about 7 mm) may be used if the pad backing is redesigned. For example, if a convex or flat shaped backing is used (as opposed to the concave backing shown in FIGS. 3 and 4), or if the elastic strap is attached to the backing by forwardly directed flanges on the backing (thus permitting the backing to be mounted closer to the eye socket while still maintaining the required pressure), a less thick pad may be used.

The use of the eyelid splint of the invention is simple and very practical. A patient now has options to use the device of the invention easily by himself. For example, a patient may remove his dressing at home, and reapply by himself for bathing the eye, applying medicine, and the like. For the physician, easy access to the eye is permitted for reexamination without the cumbersome task of changing dressings with tape, cotton pads, etc. If a sterile dressing falls on the floor when a patient removes a conventional splint, it not only becomes extremely inconvenient since a new dressing need be applied, but an opportunity for eye infection is presented. With the splint of the invention, the protective paper strip is simply peeled away from the low-peel adhesive of a replacement pad, and a replacement pad is simply attached to the rear surface of the shield. Since it is all one piece, the splint can easily be handled in removal and reapplication without dropping or even touching the sterile pad. In addition, the elastic straps need not be unfastened when the device is removed from the patient's head to change the pad. Rather, the elastic straps are simply slipped over the patient's head in fastened condition, the pad is replaced, and the splint is remounted on the eye. Since the replacement pad is identical to the pad which was removed, the splint pressure has already been perfectly adjusted to suit the wearer.

Having described several embodiments of the invention in detail, those skilled in the art will appreciate numerous modifications may be made to the device of the invention without departing from the spirit and scope thereof. Accordingly, the foregoing detailed description of these embodiments should not be considered limiting, and the invention should be defined only by the following claims.

I claim:

1. An apparatus for protecting an eye of a patient which comprises
   an eye shield member having a smooth inner surface,
   a soft resilient pad member removably secured to the smooth inner surface of the eye shield member,
   said pad member having a rear surface adapted to press against the exterior of a patient's eyelid and a forward portion secured to the eye shield member,
   said pad member having a thickness sufficient to compress the patient's eyelid and maintain it in closed position when the apparatus is worn by the patient,
   adhesive means disposed upon the forward portion of the pad member having a low-peel adhesion such that the pad member is easily removable from the eye shield member, and
   head-encircling strap means for attaching the apparatus to the head of a patient.

2. The apparatus of claim 1 wherein the pad member has a thickness of at least 7 mm.

3. The apparatus of claim 1 wherein the eye shield member has sufficient structural rigidity to bridge across the patient's facial bone structure surrounding the patient's eye.

4. The apparatus of claim 1 wherein the pad member has a thickness of at least 10 mm.

5. The apparatus of claim 1 wherein the adhesive means has a peel adhesion strength of less than about 20 oz. (PSTC-3 MOD).

6. The apparatus of claim 1 wherein the pad member is plastic foam having a compressibility of from about 5 to about 20 psi i.l.d. and has a thickness of at least 10 mm.

7. The apparatus of claim 1 wherein the eye shield member has a concave inner surface.

8. The apparatus of claim 1 wherein the eye shield member has a plurality of apertures therethrough.

9. The apparatus of claim 1 wherein the eye shield member has a curvilinear peripheral edge adapted to mount on a patient's head adjacent the bony orbital rim of the eye.

10. The apparatus of claim 1 wherein the adhesive means has a peel adhesion strength of about 16 oz. and a shear adhesion (PSTC-7 MOD) of over 100 hours.

11. An apparatus for protecting an eye of a patient which comprises
    an eye shield member having a smooth inner surface,
    a soft resilient pad member having a rear surface adapted to press against the exterior of a patient's eyelid and a forward portion secured to the eye shield member,
    said pad member comprising a flexible foam portion having a thickness of at least 7 mm, said thickness being sufficient to compress the patient's eyelid and maintain it in closed position when the apparatus is worn by the patient, and a flexible plastic film segment secured to a forward surface of the foam portion,
    a first adhesive means disposed between the plastic film segment and the foam portion,
    a second adhesive means disposed between the plastic film segment and the smooth inner surface of the eye shield member, whereby the resilient pad member is removably secured to the smooth surface of the eye shield member, and whereby
    the first adhesive means has a substantially greater adhesive strength than the second adhesive means.

12. The apparatus of claim 11 wherein the eye shield member has sufficient structural rigidity to bridge across the patient's facial bone structure surrounding the patient's eye.

13. The apparatus of claim 11 wherein the pad member has a thickness of at least 10 mm.

14. The apparatus of claim 11 wherein the second adhesive means has a peel adhesion strength of less than about 20 oz. (PSTC-3 MOD).

15. The apparatus of claim 11 wherein the pad member is plastic foam having a compressibility of from about 5 to about 20 psi i.l.d. and has a thickness of at least 10 mm.

16. The apparatus of claim 11 wherein the eye shield member has a concave inner surface.

17. The apparatus of claim 11 wherein the eye shield member has a plurality of apertures therethrough.

18. The apparatus of claim 11 wherein the eye shield member has a curvilinear peripheral edge adapted to mount on a patient's head adjacent the bony orbital rims of the eye.

19. The apparatus of claim 11 wherein the second adhesive means has a peel adhesion strength of about 16 oz. and a shear adhesion (PSTC-7 MOD) of over 100 hours.

* * * * *